(12) United States Patent
Dillon et al.

(10) Patent No.: US 12,263,255 B2
(45) Date of Patent: Apr. 1, 2025

(54) DEBRIDING WOUND DRESSING, PROCESS OF MANUFACTURE AND USEFUL ARTICLES THEREOF

(71) Applicants: Mark E. Dillon, Center Valley, PA (US); Krishna Narayanan, Pittsburgh, PA (US); Sean Michael Adams, Allentown, PA (US)

(72) Inventors: Mark E. Dillon, Center Valley, PA (US); Krishna Narayanan, Pittsburgh, PA (US); Sean Michael Adams, Allentown, PA (US)

(73) Assignee: Bio Med Sciences, Inc., Allentown, PA (US)

(*) Notice: Subject to any disclaimer, the term of this patent is extended or adjusted under 35 U.S.C. 154(b) by 60 days.

(21) Appl. No.: 16/218,197

(22) Filed: Dec. 12, 2018

(65) Prior Publication Data
US 2019/0192724 A1   Jun. 27, 2019

Related U.S. Application Data

(60) Provisional application No. 62/597,798, filed on Dec. 12, 2017.

(51) Int. Cl.
*A61L 15/38*   (2006.01)
*A61F 13/00*   (2024.01)
(Continued)

(52) U.S. Cl.
CPC ........ *A61L 15/38* (2013.01); *A61F 13/00063* (2013.01); *A61F 13/05* (2024.01);
(Continued)

(58) Field of Classification Search
CPC ...... A61F 2013/00927; A61F 13/00063; A61F 2013/00365; A61F 13/00;
(Continued)

(56) References Cited

U.S. PATENT DOCUMENTS 3,339,546 A * 9/1967 Chen ............... A61L 15/225
                                                 602/56
3,705,083 A * 12/1972 Wegman ............ C12N 9/52
                                                 435/220
(Continued)

FOREIGN PATENT DOCUMENTS

EP   0290207 A2 * 4/1988
FR   2975710 A1 * 11/2012 ............ D02G 3/36

OTHER PUBLICATIONS

Lighthouse Medical Supplies ("What is the Difference Between Woven and Nonwoven Gauze?") (Year: 2019).*
(Continued)

*Primary Examiner* — Caitlin A Carreiro
(74) *Attorney, Agent, or Firm* — John F. A. Earley, III; Harding, Earley, Follmer & Frailey, P.C.

(57) ABSTRACT

A wound dressing for active continuous debridement of devitalized tissues in non-healing wounds including diabetic ulcers, pressure ulcers, burn injuries and other etiologies, includes an active ingredient, such as collagenase, which serves to debride wounds in-situ. In one example, purified Collagenase (90% pure) was deposited onto several wound dressing materials. A key feature of this invention is that the activity level of the Collagenase used was substantially preserved.

13 Claims, 4 Drawing Sheets

(51) Int. Cl.

| | | |
|---|---|---|
| *A61F 13/05* | (2024.01) | |
| *A61F 13/06* | (2006.01) | |
| *A61F 13/15* | (2006.01) | |
| *A61F 13/36* | (2006.01) | |
| *A61F 13/511* | (2006.01) | |
| *A61F 13/53* | (2006.01) | |
| *A61L 15/22* | (2006.01) | |
| *A61L 15/26* | (2006.01) | |
| *A61L 15/42* | (2006.01) | |
| *A61L 15/44* | (2006.01) | |

(52) U.S. Cl.
CPC ...... *A61F 13/069* (2013.01); *A61F 13/15699* (2013.01); *A61F 13/36* (2013.01); *A61F 13/51113* (2013.01); *A61F 13/51121* (2013.01); *A61L 15/225* (2013.01); *A61L 15/26* (2013.01); *A61L 15/425* (2013.01); *A61L 15/44* (2013.01); *A61F 2013/00089* (2013.01); *A61F 2013/530226* (2013.01); *A61F 2013/530802* (2013.01); *A61L 2300/254* (2013.01); *A61L 2300/40* (2013.01); *A61L 2400/00* (2013.01)

(58) Field of Classification Search
CPC .. A61F 2013/00089; A61F 2013/00268; A61F 13/00068; A61F 2013/00536; A61F 13/02; A61F 13/022; A61F 13/023; A61F 13/0233; A61F 13/0216; A61F 13/0203; A61F 13/0246; A61F 13/069; A61F 13/15699; A61F 13/36; A61F 13/51113; A61F 13/51121; A61F 2013/530226; A61F 2013/530802; A61F 13/00008; A61F 13/00021; A61F 13/00089; A61F 13/0243; A61F 13/14; A61F 2013/00744; A61F 2013/15934; A61F 2013/53062; A61L 15/00; A61L 15/16; A61L 15/42; A61L 15/44; A61L 15/40; A61L 15/22; A61L 15/32; A61L 2300/00; A61L 2300/254; A61L 2300/40; A61L 15/38; A61L 15/225; A61L 15/26; A61L 15/425; A61L 2400/00; A61L 26/00; A61L 26/0066; A61M 1/0023; A61M 1/0031; A61M 27/00; A61M 1/0088; A61M 1/0092

USPC ................ 602/41–43, 45, 48; 424/445–447; 604/304; 128/888–893

See application file for complete search history.

(56) References Cited

U.S. PATENT DOCUMENTS

| | | |
|---|---|---|
| 4,832,009 A | 5/1989 | Dillon |
| 5,759,560 A | 6/1998 | Dillon |
| 2001/0024656 A1 | 9/2001 | Dillon |
| 2002/0156437 A1 | 10/2002 | McDevitt et al. |
| 2005/0159695 A1 | 7/2005 | Cullen et al. |
| 2006/0083776 A1* | 4/2006 | Bott ............... A61K 9/7084 424/445 |
| 2007/0265585 A1 | 11/2007 | Joshi et al. |
| 2011/0251574 A1 | 10/2011 | Hedrich et al. |
| 2014/0114268 A1* | 4/2014 | Auguste ............ A61F 13/022 156/182 |
| 2014/0322512 A1* | 10/2014 | Pham ................. D01F 8/16 428/220 |

OTHER PUBLICATIONS

Machine translation of FR-2975710-A1 (Year: 2012).*
Machine translation of EP 0290207 A2 (Year: 1988).*
International Search Report (copy enclosed) and Search Strategy (4 pages—copy enclosed), PCT Appln No. PCT/US2018/65263.
Written Opinion of the International Searching Authority (copy enclosed), PCT Appln. No. PCT/US2018/65263.
"What is the difference between woven and non-woven gauze?" (Lighthouse Medical Supplies Ltd) Sep. 20, 2016.
International Search Report and Search Strategy.
Written Opinion of the International Searching Authority.

* cited by examiner

DEBRIDING WOUND DRESSING, PROCESS OF MANUFACTURE AND USEFUL ARTICLES THEREOF

CROSS REFERENCE TO RELATED APPLICATION

This application claims the benefit of U.S. provisional Application No. 62/597,798, which was filed on Dec. 12, 2017 and which is incorporated herein by reference in its entirety.

BACKGROUND OF THE INVENTION

1. Field of the Invention

This invention describes a wound dressing product for active continuous debridement of devitalized tissues in non-healing wounds including diabetic ulcers, pressure ulcers, burn injuries and other etiologies. The present invention pertains to the principle of continuous wound debridement which makes necrotic tissue more susceptible for removal and hence enhances progressive wound healing. The dressing contains an active ingredient, such as collagenase which serves to debride wounds in-situ.

2. Description of the Prior Art

Wound healing is a complex process and dressings are often required to address multiple issues that healing demands. Various dressing methods have been used throughout history. In more modern times most dressings were made of cotton which was soaked with variety of agents including normal saline, sodium hypochlorite, petrolatum jelly, etc. These dressings were followed by hydrogels, alginates silicone-based composites and other technologies. In the recent past, incorporation of silver (a natural antimicrobial agent) into the various types of wound dressings has provided a major advance in the treatment of infected wounds. There are now over 1,500 dressing types that are available for clinical use. (C. Huang et al, 2014. Effect of negative pressure wound therapy on wound healing, current Problems in Surgery 51,301-331)

Necrotic tissue in a wound can delay healing of the wound significantly resulting in increased healthcare costs. Hospital acquired pressure ulcers can add significantly to the cost of patient care. It is imperative steps are taken to influence the healing process in as short of a time frame as possible. Necrotic tissue arises out of cell death and can appear dry, leathery and hard and sometimes mucoid and "stringy." Slough is typically a soft moist yellow or grey substance whereas eschar can be hard and leathery with black necrotic tissue. Depending on the depth of cell death, different tissues such as dermis, fascia, muscle, and other tissues structures may be involved. There are multiple ways to address necrotic tissue including autolytic debridement, enzymatic debridement or surgical/mechanical debridement. Regardless of the method, there is a need for continuous debridement of the necrotic eschar day to day for healing to occur. Healthy cells simply will not multiply and propagate over necrotic tissue. For this reason, enzymatic debridement is often used on partial thickness for spontaneous healing or on full thickness wounds which require skin grafting.

Closure of large wounds has been accomplished by use of Negative pressure wound therapy (NPWT). Essentially this involves use of a sponge sealed with an occlusive membrane and connected to a controlled vacuum. The process works by drainage of excess fluids from the wounds, decreasing bacterial loads and optimization of wound bed. There is also microdeformation which is caused by the force created by the collapse the foam. Because of this wound margins are approximated. The rate of closure depends on the type and thickness of the skin example, e.g. scalp skin has very different physiology than abdominal skin. However, the foam does not affect eschar which is present on the wound surface. In fact, the presence of eschar can impede the process of healing and often times eschar management becomes critical prior to even considering use of NPWT. The technology as initially pioneered by KCI (San Antonio, Texas, USA) and is commercially know as a "Wound VAC."

The main components of eschar and necrotic tissue are collagen fibers. The collagen fibers at the micron scale consists of collagen fibrils with a diameter of about 100 nm. Collagen fibrils are formed by collagen molecules with a diameter of 1.6 nm. Each collagen molecule is a triple helical protein structure that consists of three chains with a characteristic repeating sequences of the aminoacids, Glycine-Proline-Hydroxyproline (Gly-Pro-HyP). (M. D. Shoulders & R. T. Raines, 2009. Collagen structure and stability, Annual Review of Biochemistry 78, 929-958, and S. Chang & M. J. Buehler, 2014. Molecular biomechanics of collagen molecule, Materials today 17 (2) 70-76.). In humans, collagen comprises one third of the total body's protein and accounts for three quarters of the dry weight of skin. It is the most prevalent component of extracellular matrix and is surrounded by proteoglycan matrix. Normal connective tissue has collagen embedded in a matrix. In necrotic tissues collagen is aggregated in clumps without blood supply.

There are inherent matrix metallo proteinases (MMP's) in a wound site, the most important being Collagenase (MMP-1), which cleaves collagen at a single site. (M. F. Paige et al, 2002. Real time enzymatic biodegradation of collagen fibrils monitored by atomic force spectroscopy, International biodeterioration and biodegradation 50, 1-10) In addition, there are also other MMP's which may play a role. In the formation of the necrotic area in a wound there is inherent lack of functional MMP's and hence a stagnation in wound healing. Collagenases are special enzymes which degrade collagen. They cleave peptide bonds in the triple helix thereby disassociating the structural integrity of collagen fibers. Two mechanisms have been proposed to explain the collagen degradation by Collagenase: 1) Collagen molecules unfold at the cleavage site before enzyme binding, or 2) Enzymes unwind collagen molecules after binding. All types of Collagenases show preferences for different fibrillar collagen substrates. They cut the native super helix into three fourth and one fourth fragments at a single peptide bond between a Gly and Leu or Isoleu. The fragments are further degraded into a mixture of small oligopeptides. Degradation of collagen molecules is a crucial step for many biological processes including wound healing as well as many pathological processes.

Clostridial Collagenases are highly efficient enzymes degrading all types of collagen. (U. Eckhard et al, 2014. Proteomic protease specificity profiling of Clostridial Collagenases reveals their intrinsic nature as dedicated degraders of collagen, Journal of proteomics 100, 102-114) Clostridial Collagenases are approved therapeutic agents for enzymatic wound debridement. (J. Ramundo et al, 2009. Collagenase for enzymatic debridement: a systematic review, Journal of wound ostomy continence nursing 36, S4-S11) In chronic non healing wounds with severe necrotic tissue there is a need to externally supplement Collagenase to degrade the collagen fibers in the tissue to expose healable healthy tissue. Externally applied Collagenase can effectively degrade fibrous tissue. (W. D. Shingleton et al, 1996. Collagenase: a key enzyme in collagen turnover, Biochemistry and Cell Biology 74, 759-775) In other words, topically applied collagenase degrades necrotic tissue without affecting healthy viable tissue. The safety and efficacy of Collagenase ointment has been previously described. (L. Shi & D. Carson, 2009. Collagenase Santyl ointment: a selective agent for wound debridement, Journal of wound ostomy continence and nursing 36, S12-16) Extensive review suggests that enzymatic debriding agents serve as effective alternates for removing necrotic material from burns, pressure ulcers, vascular ulcers including diabetic ulcers and venous stasis ulcers. They help to debride adherent slough and eschar. (J. Ramundo & M. Gray, 2008. Enzymatic wound debridement, Journal of wound ostomy continence nursing 35 (3), 273-280) One commercially available product based on Collagenase is Santyl at 250 units/g from Smith & Nephew (London, UK).

The current practice involves use of Collagenase dispersed in petroleum jelly and applied directly to the wound site for management of necrotic tissue. Bromelain is a mixture of enzymes found in pineapples (Ananas comosus) that digest protein (proteolytic). Enzymes found in pineapple have been used for centuries in Central and South America to reduce inflammation and treat wounds. These products are typically supplied in tube containers for delivery to the wound surface. In some instances, there is significant pain associated with the use of these types of products. The amount of material used is not controlled and varies according to the person applying the dressing to the wound. The stability of this product at room temperature is delicate, and exposure to elevated temperatures in known to accelerate degradation of the enzymes and therefore activity.

Rylon® wound dressing is a wound dressing currently manufactured and marketed by the Applicant (see FIG. 1). It consists of a polyester non-woven mesh (20) coated with silicone (10) on one or both sides. The silicone is applied in thin enough layers so that the openings of the mesh are preserved, thus allowing fluid and vapor to readily pass through the dressing. The silicone coated non-woven mesh is then passed through a tunnel oven one or more times to accelerate the crosslinking of the silicone. It is used as a non-adherent wound contact layer typically in conjunction with a secondary dressing to absorb exudate produced by the wound. Rylon® wound dressing's non-adherent quality prevents secondary dressings from adhering to the wound, thereby avoiding trauma during dressing changes.

The Applicant also manufactures and markets a wound dressing under the trademark Dual-Dress™ (See FIG. 2), which is the subject of co-pending U.S. patent application Ser. No. 09/754,010, which is incorporated herein by reference. This dressing consists of a relatively thick (over 1 cm) open-cell polyurethane foam (30) bonded on one side to an occlusive membrane of silicone & polytetrafluoroethylene ("PTFE") interpenetrating polymer network polymer network ("IPN") (40). The IPN material is pigmented blue so that it is readily visible to the user. The product is typically used for covering skin graft applied to full-thickness wounds, i.e., 3rd degree burns. It is applied with the foam side against the wound, and provides a highly absorbent covering while avoiding strike-through of exudate or contamination of the wound from external sources. It also provides a bolster effect to prevent the delicate skin grafts from being disturbed during the critical initial days when the grafts are not fully vascularized and susceptible to being dislodged.

There are a number of challenges with incorporating enzymes such as collagenase directly into wound dressings—including Rylon® wound dressings and Dual-Dress™ wound dressings. As previously mentioned, enzymes are inherently temperature sensitive, thereby activity may be substantially reduced during the manufacturing process. Simply lowering process temperatures is not a satisfactory option because it necessitates a corresponding reduction in line-speed, thereby making the processing economically unfeasible. For Rylon® wound dressings, once the silicone is crosslinked, collagenase is not released from the polymer matrix thereby defeating the purpose of adding it in the first place.

Additionally, for Dual-Dress™ wound dressings the collagenase would need to be incorporated into thick foam and very little (if any) would be in direct contact with the wound.

It is believed that this invention also has an effect on fibrin and elastin.

SUMMARY OF THE INVENTION

We have unexpectedly discovered that enzymatic debriding agents can be incorporated into a wound dressing device as to debride wounds in situ.

A key feature of this invention is that the activity level of the collagenase used was substantially preserved. We were able to detect active Collagenase released from the dressings as shown in the examples below.

It is also the intent of this invention to incorporate Collagenase into wound VAC sponges which is potentially applicable to all manufacturers of wound VAC systems. In the presence of eschar, the Collagenase can serve its function and improve the effectiveness of wound VAC systems.

DETAILED DESCRIPTION OF PREFERRED EMBODIMENTS

Figure 1:
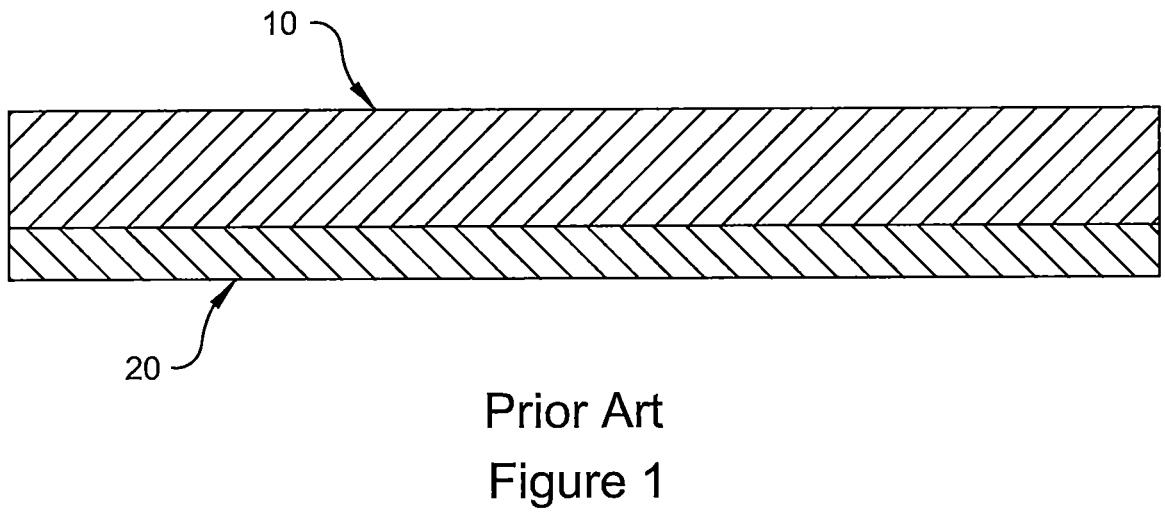
FIG. 1 shows a cross-sectional view of a Rylon® wound dressing.
Figure 2:
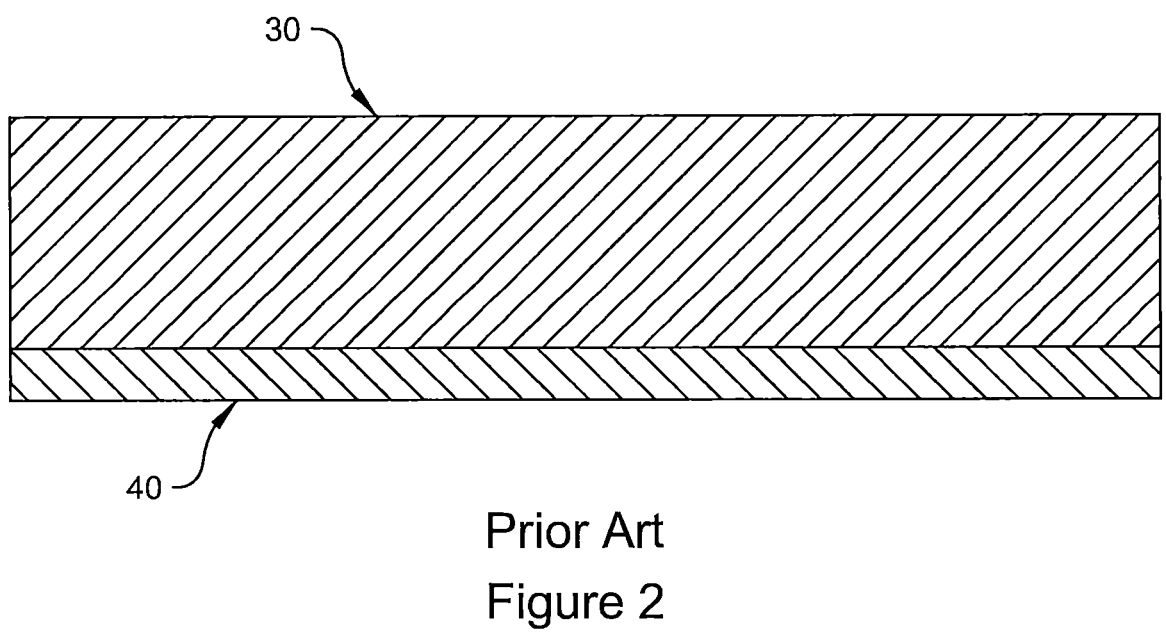
FIG. 2 shows a cross-sectional view of a Dual-Dress™ wound dressing.
Figure 3:
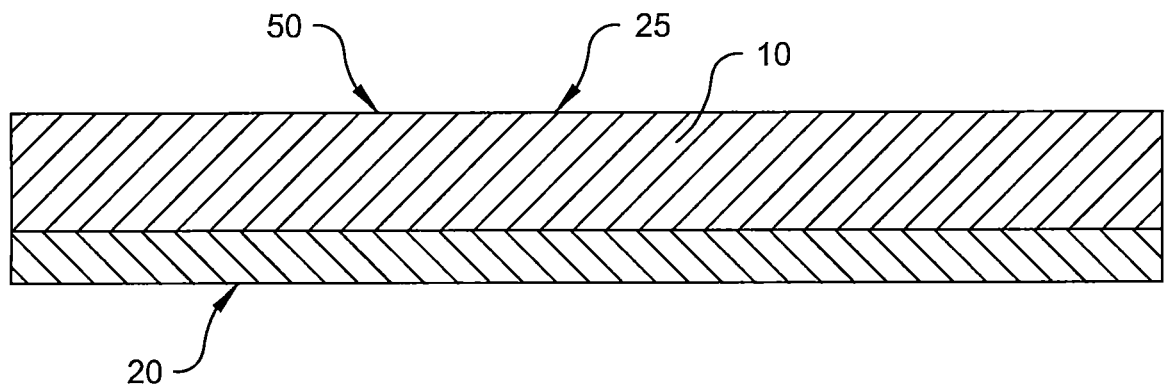
FIG. 3 shows a cross-sectional view of a preferred embodiment of the inventive wound dressing device, constructed in accordance with the invention, in which an enzymatic debriding agent (50) has been deposited into and/or onto the wound contacting surface (25) of the silicone layer (10) of the Rylon® wound dressing.
Figure 4:
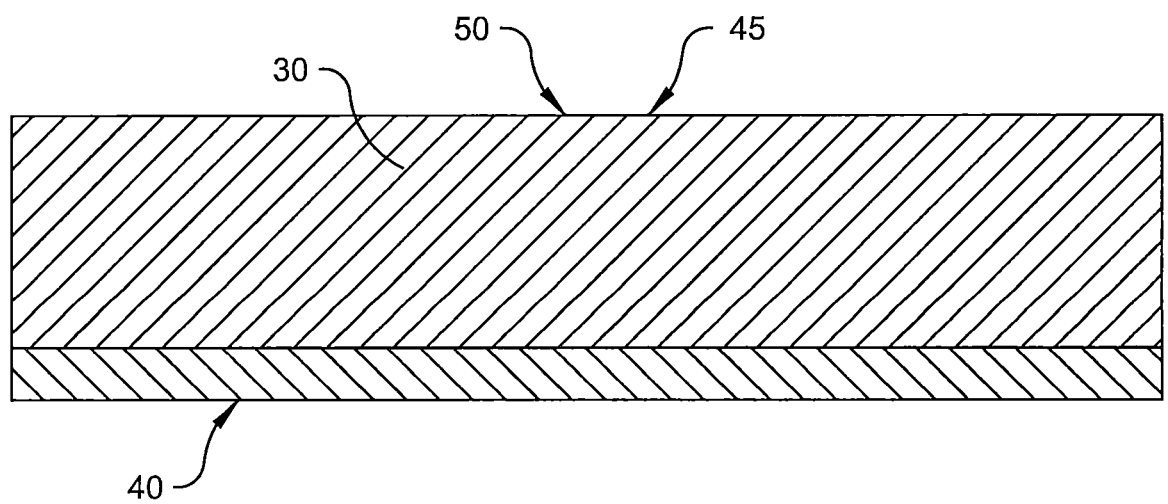
FIG. 4 shows a cross-sectional view of another preferred embodiment of the inventive wound dressing device, constructed in accordance with the invention, in which an enzymatic debriding agent (50) has been deposited into and/or onto the wound contacting surface (45) of the foam layer (30) of the Dual-Dress™ wound dressing.
Figure 5:
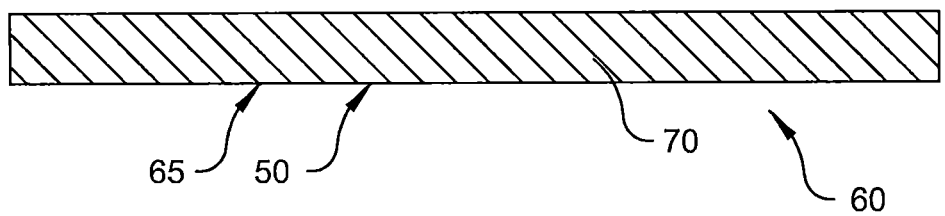
FIG. 5 is a schematic view in cross-section of a wound dressing (60) constructed in accordance with the invention, in which an enzymatic debriding agent (50) has been deposited into and/or onto the wound contacting surface (65) of the wound dressing material (70) of the wound dressing (60). Preferably, the wound dressing material is any material used to contact a wound in conventional wound dressings.
Figure 6:
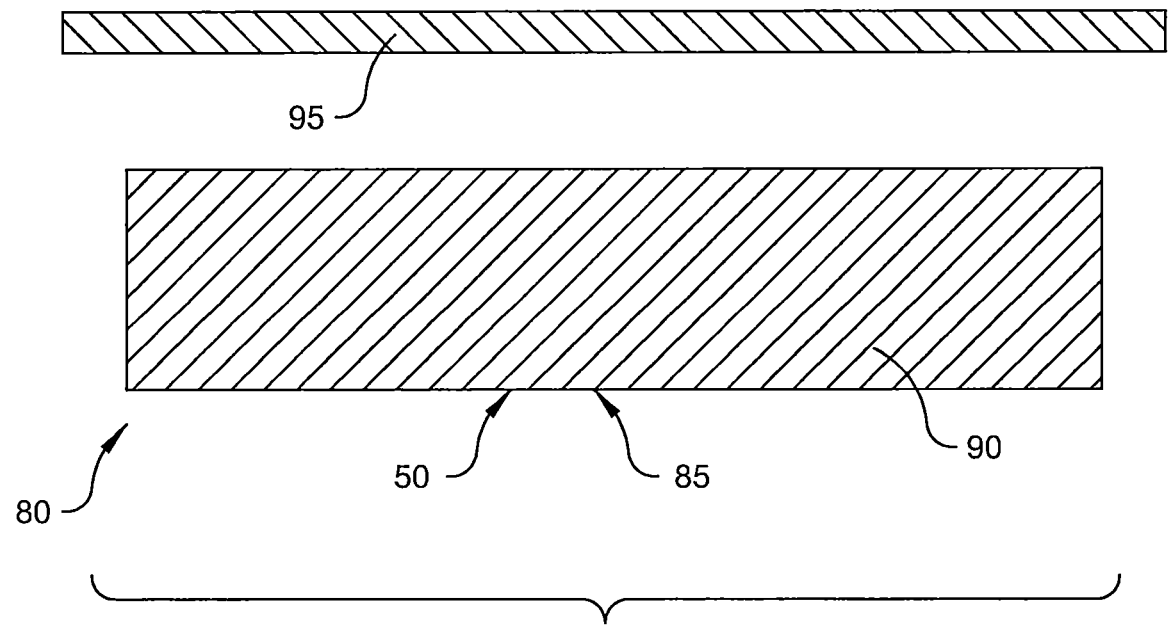
FIG. 6 is a schematic view in cross-section of a wound VAC dressing (80) constructed in accordance with the invention, in which an enzymatic debriding agent (50) has been deposited into and/or onto the wound contacting surface (85) of the sponge (90). An occlusive membrane (95) is provided for covering the sponge (90) when the wound VAC dressing is secured over a wound.
Figure 7:
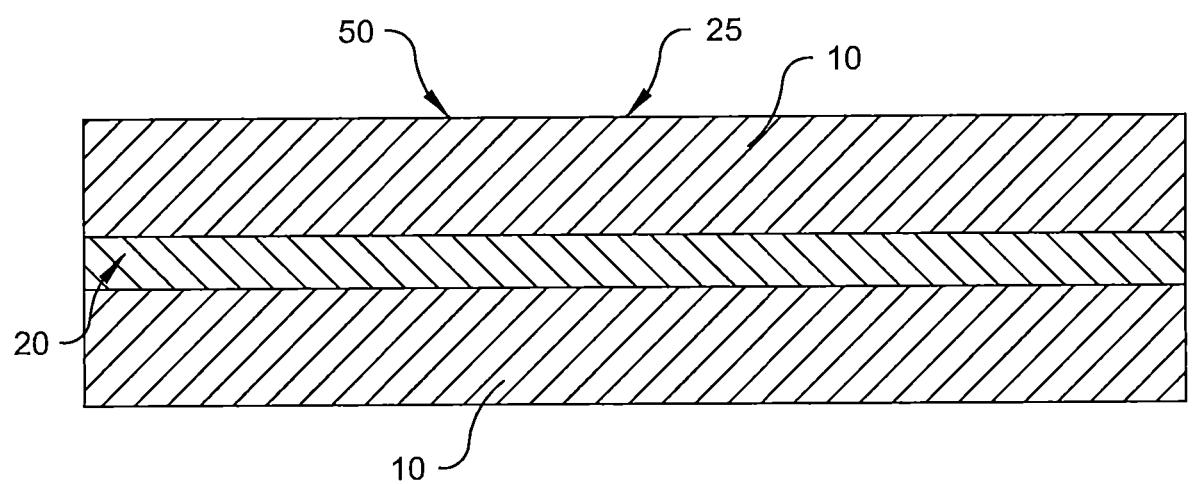
FIG. 7 shows a cross-sectional view of a preferred embodiment of the inventive wound dressing, constructed in accordance with the invention, in which an enzymatic debriding agent (50) has been deposited into and/or onto the wound contacting surface (25) of the silicone layer (10) of a Rylon® wound dressing that consists of a polyester non-woven mesh coated with silicone on both sides.

In the present invention purified Collagenase (90% pure) from Vitacyte LLC. (Indianapolis, Indiana, USA) was deposited onto several wound dressing materials. The dressing can be sized to fit the wound base so that the viable tissue is not in direct contact with active surface of the dressing. In the case of a foam dressing, the active enzyme may be applied onto the wound VAC foam of all types and materials. The active enzyme will debride the eschar at the same time as macro and microdeformational forces are actively molding the wound for effective healing. This expands the usage of wound VAC dressings where the wound base contains necrotic and eschar tissue.

The following examples are not intended to be limiting, as minor variations on these designs and processes would be obvious to those skilled in the art. Likewise, it is believed that some materials could be substituted and still achieve a substantially similar result. Additionally, there are numerous enzymes and other active ingredients that may be useful.

Example 1

Commercially available Collagenase ointment (Santyl 250 Units/g) was mixed with the silicone matrix as per standard technique. This was submitted to the supplier of the collagenase for evaluation of its release from the matrix. The activity analysis was aimed to determine that the Collagenase enzymes were present in their native state in the extract. There was difficulty in solubilization of the Collagenase for analysis. After 24 hours of extraction of Collagenase from the matrix the supernatant was analyzed and at least one form of Collagenase was found.

Example 2

We used lyophilized 90% pure Vitacyte Collagenase which was shown to be at least 10-20 times more active than Collagenase present in the Santyl. The technique was modified in the form of dusting the Collagenase on the surface of the matrix to create 3 levels of coating: "light," "medium" and "heavy." The coating weight was to determine by differential weight analysis and reported by mg/cm$^2$.

| Qualitative Coating Weight | Measured Coating Weight (mg/cm$^2$) |
|---|---|
| Low | 0.18 |
| Medium | 0.69 |
| High | 1.31 |

This was likewise submitted for Collagenase activity assays.

For the Collagenase extraction analysis 2 cm$^2$ piece from the matrix was cut and the backing was peeled off and the matrix was further cut into smaller pieces. The extraction was performed at room temperature. The extracts were then analyzed for Collagenase activity by UV spectroscopy and High Pressure Liquid Chromatography (HPLC). The low and the medium loaded extracts showed little or no intact Collagenase. The high loaded extract (1.3 mg/cm$^2$) did contain Collagenase enzymes on HPLC analysis although the recovery was very low.

Further experiments were performed with a larger sample of the matrix, as illustrated in Example 3 below.

Example 3

Collagenase extraction was performed as above on 4 cm$^2$ of each matrix of Example 2. The extraction duration was about 20 hours. The UV absorbance reading for the low and the medium coated matrices did not show any activity, which was consistent with the earlier experiment illustrated in Example 2. In this experiment, the low and medium loaded extracts showed little or no intact Collagenase (0.0248 mg/cm$^2$ for the low load matrix and 0.0431 mg cm$^2$ for the medium load matrix). With the high loaded product, there was much more enzyme protein present. The Collagenase activity was 0.427 mg/cm$^2$. HPLC analysis indicated that the bulk of the material solubilized was Collagenase which was intact and was found to have activity. The high loaded sample had the best percentage recovery of Collagenase activity in comparison to low and medium loaded matrices.

In summary, the inventive wound dressing device comprises a wound dressing, including a wound VAC dressing, that has an enzymatic debriding agent applied or deposited into and/or onto its wound contacting surface prior to use of the wound dressing on a wound. The enzymatic debriding agent may be deposited on or applied to the wound contacting surface of the wound dressing by direct application, such as by sprinkling the wound contacting surface of the wound dressing with the enzymatic debriding agent, or such as by the application of an ointment containing the enzymatic debriding agent into and/or onto the wound contacting surface of the wound dressing.

Preferably, the enzymatic debriding agent is collagenase.

In use, the inventive wound dressing device is placed on a wound for debriding the wound in-situ. Preferably, the wound dressing device is at least sized to fit the wound base.

We claim:

1. A wound dressing for active continuous debridement of devitalized tissues in non-healing wounds, comprising
   a substrate, the substrate having a non-adherent wound contacting layer having a wound contacting side, the non-adherent wound contacting layer comprising only silicone,
   the wound dressing having a wound contacting surface, the wound contacting side of the non-adherent wound contacting layer comprising the entire wound contacting surface of the wound dressing, and
   a coating of an effective amount of an enzymatic debriding agent on and being in direct contact with the wound contacting side of the non-adherent wound contacting layer,
   the enzymatic debriding agent being collagenase, and
   the collagenase being 90% pure collagenase, and the collagenase on the wound contacting side of the non-adherent wound contacting layer having a coating weight of 1.31 mg/square centimeter.

2. The wound dressing of claim 1,
   the substrate comprising a polyester non-woven mesh coated with silicone on one side, and
   the silicone comprising the non-adherent wound contacting layer.

3. The wound dressing of claim 1,
the substrate comprising a polyester non-woven mesh coated on both sides with silicone, and
the silicone on either side of the polyester non-woven mesh comprising the non-adherent wound contacting layer.

4. A wound dressing for active continuous debridement of devitalized tissues in non-healing wounds, comprising
a substrate, the substrate having a non-adherent wound contacting layer having a wound contacting side, the non-adherent wound contacting layer comprising only silicone,
the wound dressing having a wound contacting surface, the wound contacting side of the non-adherent wound contacting layer comprising the entire wound contacting surface of the wound dressing, and
a dusting of an effective amount of an enzymatic debriding agent on and being in direct contact with the wound contacting side of the non-adherent wound contacting layer,
the enzymatic debriding agent being collagenase, and
the collagenase being 90% pure collagenase, and the collagenase on the wound contacting side of the non-adherent wound contacting layer having a coating weight of 1.31 mg/square centimeter.

5. The wound dressing of claim 4,
the substrate comprising a polyester non-woven mesh coated with silicone on one side, and
the silicone comprising the non-adherent wound contacting layer.

6. The wound dressing of claim 4,
the substrate comprising a polyester non-woven mesh coated on both sides with silicone, and
the silicone on either side of the polyester non-woven mesh comprising the non-adherent wound contacting layer.

7. A wound dressing for active continuous debridement of devitalized tissues in non-healing wounds, comprising
a substrate, the substrate having a wound contacting surface, and the wound contacting surface of the substrate comprising only silicone, and
a dusting on the wound contacting surface of the substrate of an effective amount of an enzymatic debriding agent, and
the enzymatic debriding agent being collagenase,
wherein the collagenase is 90% pure collagenase, and wherein the collagenase on the substrate has a coating weight of 1.31 mg/square centimeter.

8. The wound dressing of claim 7,
the substrate comprising a polyester non-woven mesh coated with silicone on one side.

9. The wound dressing of claim 7,
the substrate comprising a polyester non-woven mesh coated on both sides with silicone.

10. A wound dressing for active continuous debridement of devitalized tissues in non-healing wounds, comprising
a substrate, the substrate having a wound contacting surface, and the wound contacting surface of the substrate comprising only silicone, and
a coating on the wound contacting surface of the substrate of an effective amount of an enzymatic debriding agent, and
the enzymatic debriding agent being collagenase,
wherein the collagenase is 90% pure collagenase, and wherein the collagenase on the substrate has a coating weight of 1.31 mg/square centimeter.

11. The wound dressing of claim 10,
the substrate comprising a polyester non-woven mesh coated with silicone on one side.

12. The wound dressing of claim 10,
the substrate comprising a polyester non-woven mesh coated on both sides with silicone.

13. A wound dressing for active continuous debridement of devitalized tissues in non-healing wounds, comprising
a non-adherent wound contacting layer having a wound contacting side,
the non-adherent wound contacting layer comprising only silicone, and
the wound contacting side of the non-adherent wound contacting layer having an effective amount of an enzymatic debriding agent on and in direct contact with the wound contacting side of the non-adherent wound contacting layer,
the enzymatic debriding agent being collagenase,
the collagenase being 90% pure collagenase, and the collagenase on the wound contacting side of the non-adherent wound contacting layer having a coating weight of 1.31 mg/square centimeter.

* * * * *